(12) United States Patent
Zhang et al.

(10) Patent No.: US 7,001,452 B2
(45) Date of Patent: *Feb. 21, 2006

(54) POLYMERIC WOOD PRESERVATIVE COMPOSITIONS

(75) Inventors: Jun Zhang, Getzville, NY (US); Robert M. Leach, Grand Island, NY (US); Paul Griffin, Cheektowaga, NY (US)

(73) Assignee: Osmose, Inc., Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/986,242

(22) Filed: Nov. 11, 2004

(65) Prior Publication Data

US 2005/0150419 A1    Jul. 14, 2005

Related U.S. Application Data

(63) Continuation-in-part of application No. 10/627,885, filed on Jul. 25, 2003, now Pat. No. 6,843,837.

(60) Provisional application No. 60/399,071, filed on Jul. 26, 2002.

(51) Int. Cl.
*A01N 33/02* (2006.01)
*A01N 25/02* (2006.01)

(52) U.S. Cl. .............. 106/18.32; 424/78.09; 424/405; 424/618; 424/630; 424/632; 424/633; 424/634; 424/637; 424/638; 424/641; 424/646; 424/650; 424/652; 424/654; 424/655; 424/682; 427/297; 427/393; 524/434

(58) Field of Classification Search ............. 106/18.32; 424/78.09, 405, 618, 630, 632, 633, 634, 424/637, 638, 641, 646, 650, 652, 654, 655, 424/682, 297, 393; 524/434
See application file for complete search history.

(56) References Cited

U.S. PATENT DOCUMENTS 5,874,025 A * 2/1999 Heuer et al. ................. 252/383
6,843,837 B1 * 1/2005 Zhang et al. ............. 106/18.32

* cited by examiner

*Primary Examiner*—Anthony J. Green
(74) *Attorney, Agent, or Firm*—Hodgson Russ LLP

(57) ABSTRACT

The present invention relates to a method and a wood preserving composition which is free of poly-aspartic acid and its derivatives and comprises mixtures of a metal compound, complexing agents selected from ethanolamines, polyethylenimine, ammonia or a mixture of these compounds, and a vinyl based polymer selected from poly(vinyl alcohol) (PVA), poly(acrylamide) (PA), poly(N-vinyl pyrrolidone) (PVP) and poly(N-isopropyl acrylamide) (PNIPAM). The resulting metal amine solution can then be used to formulate a variety of metal-based cellulosic material preserving products.

70 Claims, 4 Drawing Sheets

POLYMERIC WOOD PRESERVATIVE COMPOSITIONS

RELATED APPLICATION MATERIAL

This application is a continuation-in-part of application Ser. No. 10/627,885, filed Jul. 25, 2003, now U.S Pat. No. 6,843,837 which claims priority to provisional application Ser. No. 60/399,071, filed Jul. 26, 2002, the disclosures of which are incorporated by reference herein.

BACKGROUND

Wood preserving compositions are well known for preserving wood and other cellulose-based materials, such as paper, particleboard, textiles, rope, etc., against organisms responsible for the destruction of wood, namely fungus and insects. Many conventional wood preserving compositions comprise copper amine complexes. Copper amine complexes have been used in the past because the copper in such complexes is soluble in aqueous solutions. The copper in the copper amine complexes is typically obtained from a variety of copper bearing materials, such as copper scrap, cuprous oxide, copper carbonate, copper hydroxide, a variety of cuprous and cupric salts, and copper bearing ores. The amine in such copper amine complexes is normally obtained from an aqueous solution of ammonia and ammonium salts such as ammonium carbonate and ammonium sulfate.

A conventional method to prepare such copper amine complexes is disclosed in U.S. Pat. No. 6,340,384. In that patent, the inventor wrote, "The copper amine complex may be prepared by methods known in the art. For example, U.S. Pat. No. 4,622,248 describes forming copper amine complexes by dissolving copper oxide in ammonia in the presence of ammonium bicarbonate." Another method to form cupric oxide and cupric oxide amine complexes is disclosed in U.S. Pat. No. 5,492,681 to Pasek et al. Pasek et al. describe a process to produce cupric oxide from copper bearing materials with aqueous ammonia and an ammonium salt in the presence of oxygen to form a cupric amine compound which, upon heating, decomposes to cupric oxide, ammonia and water.

The disadvantage of using aqueous ammonia as copper solubilizing agent lies in the strong odor of ammonia. Additionally, copper ammonia preservatives can affect the appearance of the treated wood giving surface residues and undesirable color. In recent years, many amine-containing compounds, such as ethanolamines and aliphatic polyamines, have been used to replace ammonia to formulate water-soluble copper solutions. These compounds were chosen because of their strong complexing ability with copper and the absence of undesirable odor. U.S. Pat. No. 4,622,248 discloses a method of preparing copper amine complexes by dissolving a mixture of copper carbonate [$CuCO_3$] and copper hydroxide [$Cu(OH)_2$] in ethanolamine and water. The complexing amine and copper combine stoichiometrically in a 4 to 1 (molar ratio) and thus the weight ratio of reagents will be different for each complexing amine. However, copper amine based preservatives, such as copper monoethanolamine (Cu-MEA), have higher copper loss due to leaching as compared to a traditional copper based preservative chromated copper arsenic (CCA). The high copper leaching in Cu-MEA is believed to be due to the strong complex which forms between the cupric ion and monoethanolamine (MEA). For example, more than 25% of copper present in the treated wood can be leached out when wood is treated with a Cu-MEA solution containing 0.5% copper. Although not desiring to be bound by any particular theory, the inventors believe that as the amine compound, such as MEA, is leached from the treated material, the strong complex between Cu-MEA results in the leaching of copper along with the leached MEA.

In an attempt to remedy the leaching of copper alkanolamine complexes from treated wood, U.S. Pat. No. 5,874,025 requires the addition of polyaspartic acid, its salts, or its derivatives in the preparation of a wood preservative which exhibits reduced leaching of alkanolamine. However, the polyaspartic acid is used at least partially instead of the alkanolamine, with the formation of the biocidal copper alkanolamine complex partially or completely eliminated.

U.S. Pat. No. 5,186,947 also discloses a method of preparing water soluble copper complexes using polyamines as the solubilizing agents for copper. In this invention, aliphatic acids are used in the formulations to improve the fixation and reduce the leaching of copper from wood. This patent also teaches that polyacrylic acids may be added to copper-polyethylenimine (Cu-PEI) formulations. We have discovered that the addition of polyacrylic acid to Cu-PEI results in the formation of a copper precipitate. The precipitation of copper from a wood preservative formulation is undesirable because it reduces the amount of copper present in solution which is able to penetrate into the wood. Additionally, precipitated copper will remain on the surface of the wood, potentially contributing to an uneven surface appearance of the treated wood. This is undesirable in providing an aqueous wood preservative formulation useful in providing wood products that are aesthetically acceptable to the public, yet preserved from the destructive agencies of wood.

Accordingly, the discovery that certain vinyl based polymers aid in decreasing the leaching of metal from treated wood while still providing clear aqueous formulations was entirely unexpected. Thus, the need to provide aqueous copper amine complexes that are suitable for use to treat wood, yet minimize the copper leaching from treated wood when exposed to water and do not result in precipitation is addressed by the incorporation of polyethylenimine and the vinyl based polymers poly(vinyl alcohol), polyacrylamide, poly(N-vinyl pyrrolidone), and poly(N-isopropyl acrylamide) into copper amine formulations.

SUMMARY

The present invention relates to a method and a wood preserving composition which comprises mixtures of a preservative metal compound in a preservative amount, complexing agents selected from ethanolamines, polyethylenimine, ammonia or a mixture of these compounds, and a vinyl based polymer selected from poly(vinyl alcohol) (PVA), poly(acrylamide) (PA), poly(N-vinyl pyrrolidone) (PVP) and poly(N-isopropyl acrylamide) (PNIPAM). The resulting metal amine solution can then be used to formulate a variety of metal-based cellulosic preserving products which do not form precipitates.

Therefore, in one embodiment, provided herein is an aqueous preservative composition for treating cellulose based products including wood comprising a preservative metal selected from the group consisting of copper, cobalt, aluminum, iron, lead, tin, cadmium, nickel, chromium, zinc, silver and mixtures thereof in a preservative amount; a non-polymeric amine compound in an amount sufficient to solubilize the preservative metal; a polymeric amine compound such as a polyethylenimine compound in an amount sufficient to form a chelation complex with the metal; and a vinyl based polymer selected from the group consisting of poly(vinyl alcohol), polyacrylamide, poly(N-vinyl pyrrolidone), poly(N-isopropyl acrylamide) and mixtures thereof. This composition is free of poly-aspartic acid or its derivatives and provides an aqueous preservative composition wherein no precipitate is present. In one embodiment, the aqueous preservative composition comprises between about 0.01% and about 15% by weight solubilized copper; between about 0.15% and about 10% by weight non-polymeric amine; between about 0.01% and about 40% by weight polyethylenimine having a number average molecular weight between about 100 and about 70,000; and between about 0.01% and about 8% poly(vinyl alcohol).

In another embodiment, provided is an aqueous preservative composition comprising a preservative metal, a polymeric amine or a non-polymeric amine; and a vinyl based polymer. In one embodiment, the preservative composition comprises between about 0.01% and about 15% by weight solubilized copper; between about 0.15% and about 50% by weight non-polymeric amine; and between about 0.01% and about 30% poly(vinyl alcohol). In another embodiment, the preservative composition comprises between about 0.01% and about 15% by weight solubilized copper; between about 0.01% and about 40% by weight polymeric amine; and between about 0.01% and about 30% poly(vinyl alcohol).

Also provided herein is a method for treating a cellulose based product including wood by applying to the cellulose based product an aqueous preservative composition for treating cellulose based products including wood prepared according to the invention herein.

DETAILED DESCRIPTION

Figure 1:
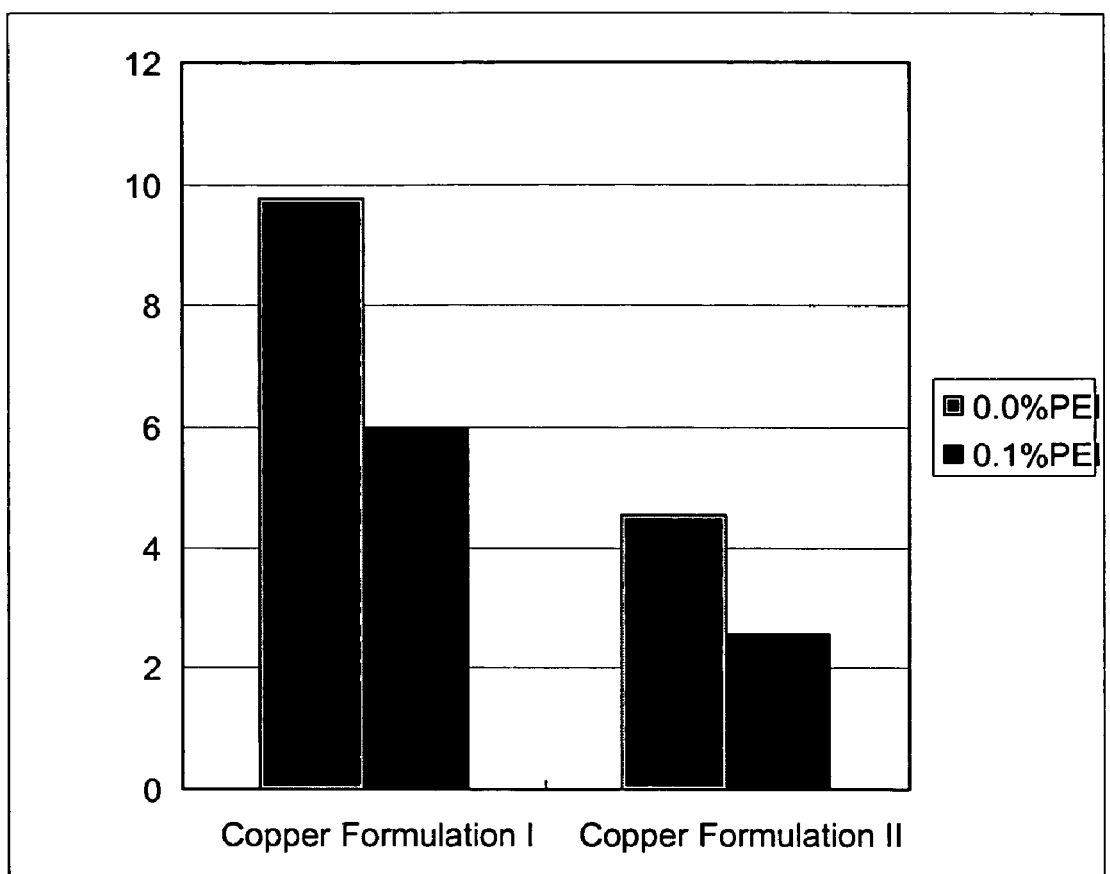
FIG. 1 is a chart showing the effect of the addition of PEI on the leaching of copper from wood.

Unless specifically stated otherwise, for example, as in the examples, all numerical values contained herein are intended to be modified by the term "about." Also, unless specifically stated otherwise, all percent values contained within are weight percent.

American Wood-Preservers' Association (AWPA) Standard E11-97 "Standard Method of Determining the Leachability of Wood Preservatives" was used to evaluate the leaching of copper from the treated wood. The results of the leaching evaluations are contained in FIGS. 1–4.

All materials used in the preparation of the wood preservative compositions according to the invention herein are readily available from commercial suppliers.

A method for the preparation of a preservative metal amine complex solution is provided that, in a preferred embodiment, efficiently reduces the leaching of metal from treated wood and does not result in the formation of precipitates. For purposes of this application, the metal amine solution is obtained from a metal bearing material that is normally soluble or insoluble in water, for example, copper, cobalt, aluminum, iron, lead, tin, cadmium, nickel, chromium, silver and zinc. The preferred metal bearing material is copper. The preservative compositions of the present invention do not contain poly-aspartic acid or its derivatives.

The amount and concentration of workable treating solution applied to a particular substrate will depend upon many factors such as the nature of the substrate (e.g., species of wood), its end use, its geographic location, the method of application and the nature of the attack to be prevented. A preservative is usually applied to a substrate in a quantity sufficient to produce a desired preservative end point and thus, actual quantities may vary broadly. In general, an effective preservative treating solution will contain from 0.01% to 15% of preservative metal salt, depending upon the salt selected. More commonly this range will vary from between 0.5% to 10% based on the preservative metal salt content.

In preparing these solutions for application to a substrate, a concentrated stock solution of preservative metal salt is first made or is obtained as a commercial preparation and is thereafter combined with a solution of vinyl based polymer and optionally diluted to a final working solution having the desired concentration. Of course, because the molecular weights of the various metals and metal compounds will be different, the weight percent of metal compound present in the metal complex solutions of the invention herein will depend upon which metal or metal compound is selected. The selection of a particular metal or metal compound is within the purview of one of ordinary skill in the art. For example, when the metal compound is copper carbonate, between 0.09% to 25.0% may be used.

Methods for solubilizing metals are well known to those of ordinary skill in the art. For example, a copper concentrate solution is prepared by mixing water with all the amine ligands or chelating agents first followed by adding copper compounds and stirring the mixture for about 0.5 hours to 6 hours depending upon the copper source. The final product may be pH adjusted by using carbon dioxide.

A workable solution is prepared by diluting the solubilized metal concentrate. The vinyl based polymer is added to the solubilized metal concentrate solution as a liquid solution along with water as needed for dilution. The vinyl based polymer is either obtained commercially as a solution or, more preferably, is obtained from a commercial supplier in dry form and formed into a solution according to the manufacturer's guidelines. The solubilized metal concentrate solution and vinyl based polymer solution may be combined with water as needed immediately prior to application to the substrate being treated.

An exemplary method to prepare the solubilized metal concentrate solution uses water soluble or water insoluble copper metal and copper compounds, such as copper sulfate, copper acetate, copper formate, copper chloride, copper nitrate, basic copper carbonate, copper hydroxide, copper oxide, cupric oxide, cuprous oxide, copper borates, etc. These copper compounds are normally prone to form water soluble copper complexes with non-polymeric amine containing organic compounds. Although the preferred non-polymeric amine containing compounds are ethanolamines which possess the structure as shown below, other amines that can also be used are diethanolamine, triethanolamine, ethylamine, diethylamine, ethylenediamine, etc.

Copper or copper compounds generally also have significant solubilities in polymeric amines, such as polethylenimine. Thus, the copper or copper compounds can be solubilized in the polymeric amine component which is particularly convenient if the non-polymeric amine component is omitted.

The structure of preferred ethanolamines is provided below:

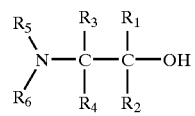

wherein $R_1$, $R_2$, $R_3$, $R_4$, $R_5$, $R_6$ independently=H, —$CH_3$, or —$C_2H_5$.

The weight percent of the non-polymeric amine containing compound will vary depending upon which non-polymeric amine containing compound is used. For example, when the non-polymeric amine containing compound is monoethanolamine, between 0.15% and 7.20% can be used. When more than one non-polymeric amine containing compound is used in the metal complex solutions of the invention herein, the total non-polymeric amine containing compound may be as much as 10.0%.

However, if the polymeric amine compound is omitted, the aqueous preservative composition preferably comprises between about 0.15% and about 50% by weight non-polymeric amine.

For economic reasons, small amounts of ammonium hydroxide or other ammonia salts such as ammonium bicarbonate, ammonium carbonate, ammonium sulfate, ammonium phosphate, etc. may be used to replace part of the ethanolamine. When used, between 0.02% and 0.6% of ammonium compound can be used to replace part of the ethanolamine.

Polyethylenimine (PEI) is a polymeric amine complexing agent. PEI can be characterized by the repeating chemical unit denoted as —[$CH_2$—$CH_2$—NH]—. The amine groups in PEI are either primary, secondary or tertiary amine groups in the approximate ratio 1:2:1 with a branching site every 3–3.5 nitrogen atoms along any given chain segment. PEI is prepared for example by the ring opening polymerization of ethylenimine (or aziridine) catalyzed by an acid. The high degree of branching is thought to be due to the chain transfer reaction of amine groups with the quaternary aziridinium ion. The number-average molecular weight (determined by Gel permeation Chromatography (GPC)) of PEI suitable for complexing copper ranges from 100 to 70,000.

A variety of polymeric amine compounds can be used in the wood preservative formulation of the present invention. However, polyethylenimine (PEI) is preferred. PEI can form chelating complexes with copper in cupric form. In most research on the subject, a 3:1 complexation ratio of PEI to copper has been proposed. A very important aspect of PEI is that this polymeric material has many cationic amine groups that are available for reaction with anionic substrates, such as cellulose or lignin in wood. Therefore, PEI can not only complex with copper to form water soluble complexes, it can also fix these complexes to the wood matrix. To reduce the viscosity of formulations and for economic purpose, PEI is often used as a ligand to replace part of the ethanolamines, with or without ammonia, to form copper complexes. PEI can also be used as an additive to the already formed copper amine complexes. Addition of PEI to the copper formulations reduces the copper leaching from treated wood by 50% as illustrated in FIG. 1.

The concentration of PEI can vary with the applications. For example, when PEI is used as a complexing agent to form copper complexes, with or without the use of other amine ligands, concentrations of PEI vary from 1.0% to 40.0%. When PEI is used as an additive to the formed copper amine solutions, the concentration of PEI can vary from 0.01% to 2.0%.

Copper leaching from treated wood is greatly reduced when certain vinyl based polymers are added to the copper amine formulations. Vinyl based polymers which do not result in the formation of copper precipitates when used at workable concentrations are poly(vinyl alcohol), polyacrylamide, poly(N-vinyl pyrrolidone), and poly(N-isopropyl acrylamide). The general structure of these polymers is given below:

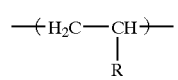

wherein R=—$CONH_2$, —$CONHCH(CH_3)_2$,

—OH, and —$CONH_2$. The preferred vinyl based polymer is poly(vinyl alcohol) (PVA).

Figure 2:
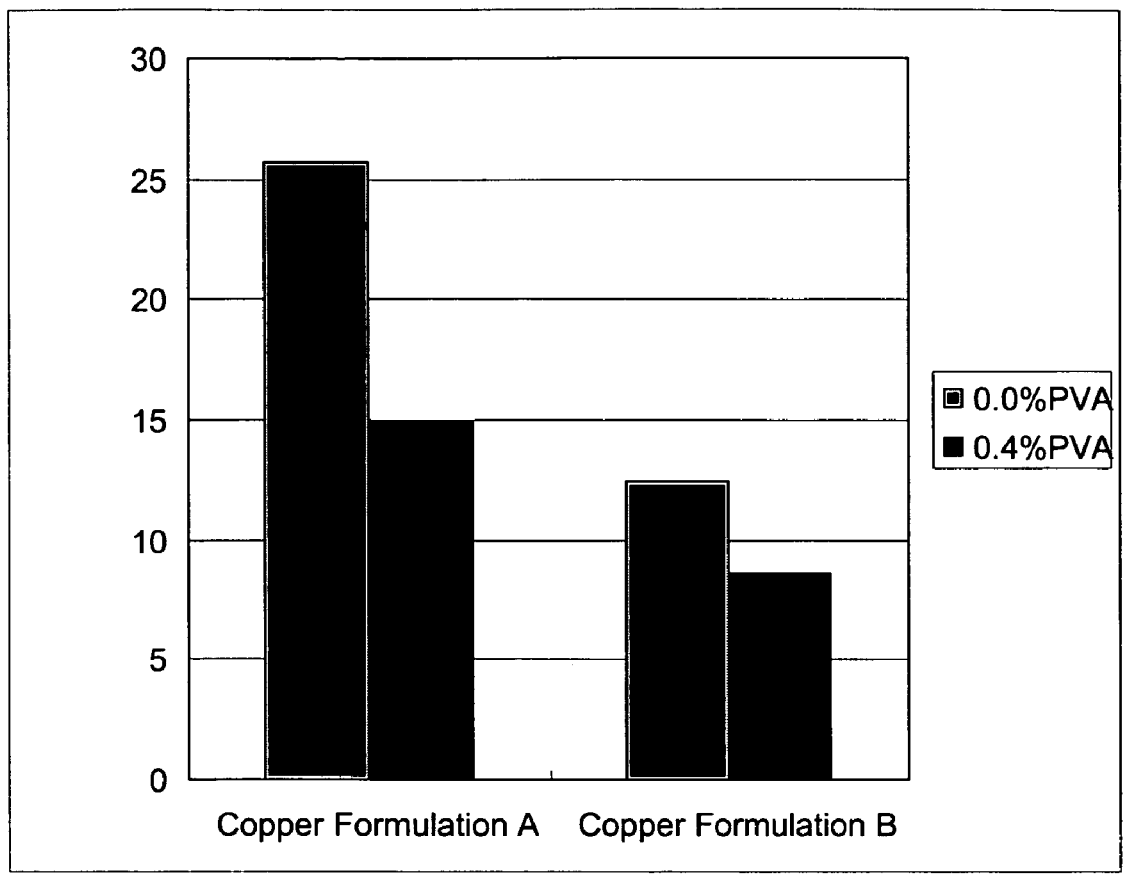
FIG. 2 is a chart showing the effect of poly vinyl alcohol on the leaching of copper.

PVA is formed, for example, from the polymerization of vinyl acetate monomer followed by hydrolysis using sodium hydroxide. The degree of polymerization suitable for this application is between 2 and 5000. The degree of hydrolysis varies from 10% to 100%. Concentrations of copper-fixing vinyl based polymer vary from 0.01% to 8.0% with 0.1%–1.0% being the preferred range. FIG. 2 demonstrates that the copper leaching from wood is reduced by about 40% when PVA is added to the copper solutions. Concentrations of vinyl based polymer greater than 8% will tend to result in the formation of copper precipitates in the final treating solution.

Figure 3:
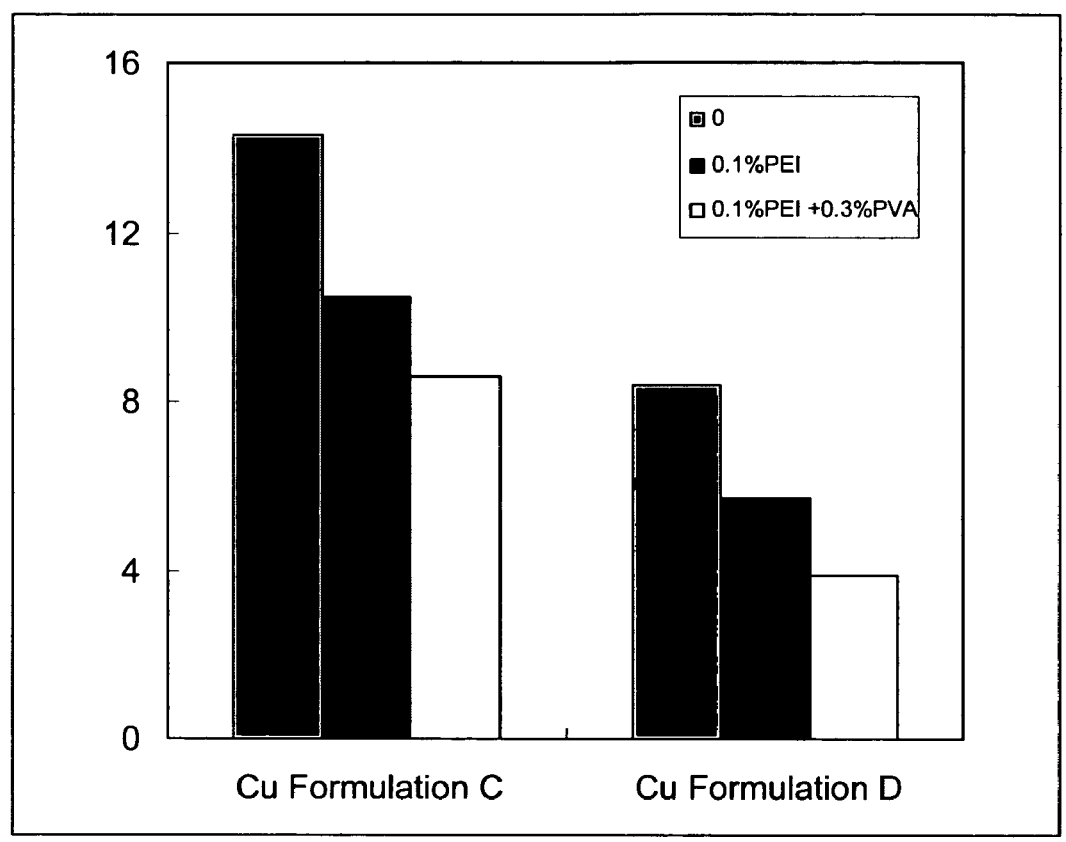
FIG. 3 is a chart showing the effect of combining polyethylenimine and poly (vinyl alcohol) in a wood preservative on the leaching of copper.

The leaching of copper from the treated wood can be further reduced by combining the polymeric amine compound and the vinyl-based polymer compound, as shown in FIG. 3 for PEI and PVA.

Figure 4:
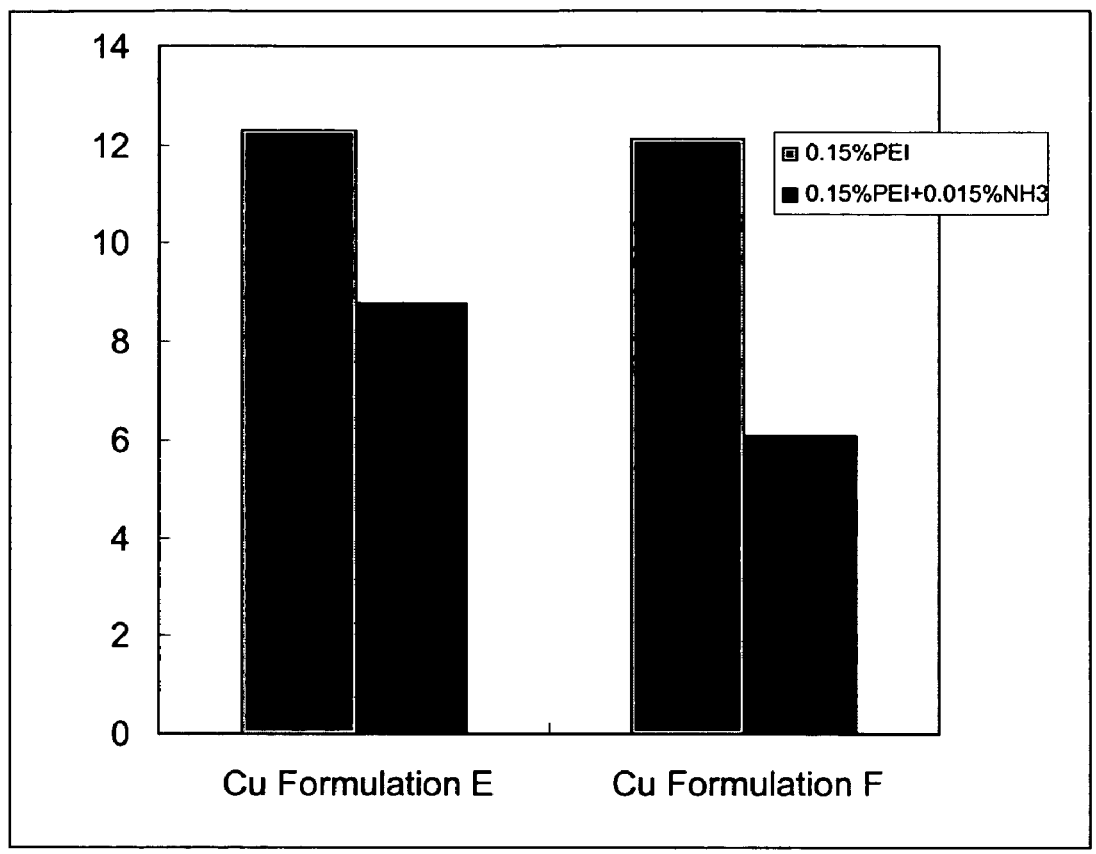
FIG. 4 is a chart showing the effect of combining polyethylenimine and ammonia in a wood preservative on the leaching of copper.

It has also been discovered that the addition of a small amount of ammonia to in FIG. 4 for PVA and PEI, further reduces the leaching of copper leaching from wood. The amount of ammonia added to the metal complex solution will be between 0.02% and 3.0%.

The resulting copper amine solution can be mixed with a variety of biocides such as fungicides and insecticides to produce a formulation suitable for the preservation of wood and other cellulose-based materials. Typical biocides that can be used for this formulation are fungicides such as azoles, quaternary ammonium compounds, etc. as well as various insecticides.

The treating solution may be applied, for example, to wood by dipping, soaking, spraying, brushing, or any other well known means. Vacuum and/or pressure techniques may also be used to impregnate the wood in accord with this invention including both the "Empty Cell" process and the "Full Cell" process which are well known to those of ordinary skill in the art.

The invention will be better understood by way of the following examples and comparative examples which are intended to illustrate but not limit the scope of the claims. Examples 1–4 are workable solutions containing polyacrylamide. Examples 5–8 are workable solutions containing poly(vinyl pyrrolidone). Examples 9–16 are workable solutions containing poly(vinyl alcohol). Examples 17–29 are metal concentrate formulations which can be mixed with solutions of vinyl based polymers to form workable solutions. The metal concentrate formulations can be optionally diluted with water prior to making workable solutions. The workable solutions can be further combined with co-biocides to prepare wood preserving treating solutions.

EXAMPLES OF POLYACRYLAMIDE WORKABLE SOLUTIONS: EXAMPLES 1–4

Example 1

| Ingredient | Percent |
|---|---|
| PEI Mw. = 10,000 | 0.08 |
| Monoethanolamine | 0.49 |
| Ammonia | 0.07 |
| Basic copper carbonate | 0.45 |
| Polyacrylamide Mw. = 1,500 | 0.25 |
| Water | 98.66 |

Appearance - Clear

Example 2

| Ingredient | Percent |
|---|---|
| PEI Mw. = 10,000 | 0.08 |
| Monoethanolamine | 0.49 |
| Ammonia | 0.07 |
| Basic copper carbonate | 0.45 |
| Polyacrylamide Mw. = 1,500 | 0.50 |
| Water | 98.41 |

Appearance - Clear

Example 3

| Ingredient | Percent |
|---|---|
| PEI Mw. = 10,000 | 0.16 |
| Monoethanolamine | 0.98 |
| Ammonia | 0.14 |
| Basic copper carbonate | 0.91 |
| Polyacrylamide Mw. = 1,500 | 0.25 |
| Water | 97.56 |

Appearance - Clear

Example 4

| Ingredient | Percent |
|---|---|
| PEI Mw. = 10,000 | 0.16 |
| Monoethanolamine | 0.98 |
| Ammonia | 0.14 |
| Basic copper carbonate | 0.91 |
| Polyacrylamide Mw. = 1,500 | 0.50 |
| Water | 97.31 |

Appearance - Clear

EXAMPLES OF POLY(VINYL PYRROLIDONE) WORKABLE SOLUTIONS: EXAMPLES 5–8

Example 5

| Ingredient | Percent |
|---|---|
| PEI Mw. = 10,000 | 0.08 |
| Monoethanolamine | 0.49 |
| Ammonia | 0.07 |
| Basic copper carbonate | 0.45 |
| Poly(vinyl pyrrolidone) Mw. = 55,000 | 0.25 |
| Water | 98.66 |

Appearance - Clear

Example 6

| Ingredient | Percent |
|---|---|
| PEI Mw. = 10,000 | 0.08 |
| Monoethanolamine | 0.49 |
| Ammonia | 0.07 |
| Basic copper carbonate | 0.45 |
| Poly(vinyl pyrrolidone) Mw. = 55,000 | 0.50 |
| Water | 98.41 |

Appearance - Clear

Example 7

| Ingredient | Percent |
|---|---|
| PEI Mw. = 10,000 | 0.16 |
| Monoethanolamine | 0.98 |
| Ammonia | 0.14 |
| Basic copper carbonate | 0.91 |
| Poly(vinyl pyrrolidone) Mw. = 55,000 | 0.25 |
| Water | 97.56 |

Appearance - Clear

Example 8

| Ingredient | Percent |
|---|---|
| PEI Mw. = 10,000 | 0.16 |
| Monoethanolamine | 0.98 |
| Ammonia | 0.14 |
| Basic copper carbonate | 0.91 |
| Poly(vinyl pyrrolidone) Mw. = 55,000 | 0.50 |
| Water | 97.31 |

Appearance - Clear

EXAMPLES OF POLY(VINYL PYRROLIDONE) WORKABLE SOLUTIONS: EXAMPLES 9–16

Example 9

| Ingredient | Percent |
|---|---|
| Monoethanolamine | 1.71 |
| Basic copper carbonate | 1.01 |
| PVA, Mw. = 15,000 | 0.20 |
| Water | 97.08 |

Appearance - Clear

Example 10

| Ingredient | Percent |
| --- | --- |
| Monoethanolamine | 1.40 |
| N-methylethanolamine | 0.51 |
| Basic copper carbonate | 0.09 |
| PVA, Mw. = 15,000 | 0.40 |
| Water | 97.60 |

Appearance - Clear

Example 11

| Ingredient | Percent |
| --- | --- |
| PEI, Mw. = 5000 | 0.69 |
| Monoethanolamine | 1.32 |
| Basic copper carbonate | 1.01 |
| PVA, Mw. = 20,000 | 0.40 |
| Water | 96.58 |

Appearance - Clear

Example 12

| Ingredient | Percent |
| --- | --- |
| PEI Mw. = 10,000 | 0.69 |
| Monoethanolamine | 1.32 |
| Basic copper carbonate | 1.01 |
| PVA, Mw. = 15,000 | 0.40 |
| Water | 96.58 |

Appearance - Clear

Example 13

| Ingredient | Percent |
| --- | --- |
| PEI Mw. = 70,000 | 0.40 |
| Monoethanolamine | 1.21 |
| Ammonia | 0.03 |
| Basic copper carbonate | 0.09 |
| PVA, Mw. = 15,000 | 0.40 |
| Water | 97.87 |

Appearance - Clear

Example 14

| Ingredient | Percent |
| --- | --- |
| PEI Mw. = 5,000 | 0.17 |
| Monoethanolamine | 0.47 |
| Ammonia | 0.03 |
| Basic copper carbonate | 0.45 |
| PVA, Mw. = 15,000 | 0.40 |
| Water | 98.48 |

Appearance - Clear

Example 15

| Ingredient | Percent |
| --- | --- |
| PEI Mw. = 10,000 | 0.38 |
| Monoethanolamine | 1.05 |
| Ammonia | 0.07 |
| Basic copper carbonate | 1.01 |
| PVA, Mw. = 15,000 | 0.40 |
| Water | 97.09 |

Appearance - Clear

Example 16

| Ingredient | Percent |
| --- | --- |
| PEI Mw. = 70,000 | 0.19 |
| Monoethanolamine | 0.53 |
| Ammonia | 0.04 |
| Basic copper carbonate | 0.50 |
| PVA, Mw. = 15,000 | 0.40 |
| Water | 98.34 |

Appearance - Clear

EXAMPLES OF PEI METAL CONCENTRATE FORMULATIONS: EXAMPLES 17–29

Example 17

| Ingredient | Percent |
| --- | --- |
| PEI Mw. = 5000 | 12.5 |
| Monoethanolamine | 24.0 |
| Basic copper carbonate | 18.2 |
| Water | 45.3 |

Appearance - Clear

Example 18

| Ingredient | Percent |
| --- | --- |
| PEI Mw. = 10,000 | 12.5 |
| Monoethanolamine | 24.0 |
| Basic copper carbonate | 18.2 |
| Water | 45.3 |

Appearance - Clear

Example 19

| Ingredient | Percent |
| --- | --- |
| PEI Mw. = 10,000 | 6.6 |
| Monoethanolamine | 24.0 |
| Basic copper carbonate | 18.2 |
| Water | 51.2 |

Appearance - Clear

Example 20

| Ingredient | Percent |
|---|---|
| PEI Mw. = 10,000 | 6.6 |
| Monoethanolamine | 14.4 |
| N-Methylethanolamine | 11.8 |
| Basic copper carbonate | 18.2 |
| Water | 49.0 |

Appearance - Clear

Example 21

| Ingredient | Percent |
|---|---|
| PEI Mw. = 10,000 | 6.6 |
| Monoethanolamine | 14.4 |
| N,N-Dimethylethanolamine | 14.0 |
| Basic copper carbonate | 18.2 |
| Water | 46.8 |

Appearance - Clear

Example 22

| Ingredient | Percent |
|---|---|
| PEI Mw. = 6,000 | 6.6 |
| Monoethanolamine | 14.4 |
| N-Ethylethanolamine | 14.0 |
| Basic copper carbonate | 18.2 |
| Water | 46.8 |

Appearance - Clear

Example 23

| Ingredient | Percent |
|---|---|
| PEI Mw. = 8,000 | 6.6 |
| Monoethanolamine | 14.4 |
| Monoisopropanolamine | 11.8 |
| Basic copper carbonate | 18.2 |
| Water | 49.0 |

Appearance - Clear

Example 24

| Ingredient | Percent |
|---|---|
| PEI Mw. = 5,000 | 6.6 |
| Monoethanolamine | 22.0 |
| Ammonia | 0.6 |
| Basic copper carbonate | 18.2 |
| Water | 52.6 |

Appearance - Clear

Example 25

| Ingredient | Percent |
|---|---|
| PEI Mw. = 10,000 | 6.6 |
| Monoethanolamine | 22.0 |
| Ammonia | 0.6 |
| Basic copper carbonate | 18.2 |
| Water | 52.6 |

Appearance - Clear

Example 26

| Ingredient | Percent |
|---|---|
| PEI Mw. = 70,000 | 6.6 |
| Monoethanolamine | 22.0 |
| Ammonia | 0.6 |
| Basic copper carbonate | 18.2 |
| Water | 52.6 |

Appearance - Clear

Example 27

| Ingredient | Percent |
|---|---|
| PEI Mw. = 5,000 | 7.0 |
| Monoethanolamine | 19.2 |
| Ammonia | 1.3 |
| Basic copper carbonate | 18.2 |
| Water | 54.3 |

Appearance - Clear

Example 28

| Ingredient | Percent |
|---|---|
| PEI Mw. = 10,000 | 7.0 |
| Monoethanolamine | 19.2 |
| Ammonia | 1.3 |
| Basic copper carbonate | 18.2 |
| Water | 54.3 |

Appearance - Clear

Example 29

| Ingredient | Percent |
|---|---|
| PEI Mw. = 70,000 | 7.0 |
| Monoethanalamine | 19.2 |
| Ammonia | 1.3 |
| Basic copper carbonate | 18.2 |
| Water | 54.3 |

Appearance - Clear

Comparative Examples

The compositions shown in the following comparative examples result in a cloudy solution and the presence of white precipitate.

Comparative Example 1

| Ingredient | Percent |
| --- | --- |
| PEI Mw. = 10,000 | 0.08 |
| Monoethanolamine | 0.49 |
| Ammonia | 0.07 |
| Basic copper carbonate | 0.45 |
| Poly(acrylic acid)Mw. = 2,000 | 0.18 |
| Water | 98.73 |

Appearance - Cloudy

Comparative Example 2

| Ingredient | Percent |
| --- | --- |
| PEI Mw. = 10,000 | 0.08 |
| Monoethanolamine | 0.49 |
| Ammonia | 0.07 |
| Basic copper carbonate | 0.45 |
| Poly(acrylic acid)Mw. = 2,000 | 0.36 |
| Water | 98.55 |

Appearance - Cloudy

Comparative Example 3

| Ingredient | Percent |
| --- | --- |
| PEI Mw. = 10,000 | 0.16 |
| Monoethanolamine | 0.98 |
| Ammonia | 0.14 |
| Basic copper carbonate | 0.91 |
| Poly(acrylic acid)Mw. = 2,000 | 0.18 |
| Water | 97.63 |

Appearance - Cloudy

Comparative Example 4

| Ingredient | Percent |
| --- | --- |
| PEI Mw. = 10,000 | 0.16 |
| Monoethanolamine | 0.98 |
| Ammonia | 0.14 |
| Basic copper carbonate | 0.91 |
| Poly(acrylic acid)Mw. = 2,000 | 0.36 |
| Water | 97.45 |

Appearance - Cloudy

In addition, various known additives may be combined with the preservative compositions formulated according to the present invention without substantially affecting the preservative capacity of the present composition. For instance, coloring agents, waxes, resins, aqueous solutions, various emulsions and other ingredients may be added to the present composition where such additional properties are desirable.

A wide variety of woods can be preserved in accordance with this invention, including hard and/or softwoods. Many other types of cellulose based materials including paper, particle board, textiles, rope and other such well known cellulose by-products may also be treated with this preservative composition, provided the material is capable of withstanding the treatment process.

It is to be fully understood that all of the foregoing examples are intended to be merely illustrative and not to be construed or interpreted as being restrictive or otherwise limiting of the present invention, excepting as set forth and defined in the hereto appended claims.

What is claimed is:

1. An aqueous preservative composition for treating a cellulose-based product, said composition comprising:
   a preservative metal selected from the group consisting of copper, cobalt, aluminum, iron, lead, tin, cadmium, nickel, chromium, silver, zinc and mixtures thereof in a preservative amount;
   a non-polymeric amine compound in an amount sufficient to solubilize the preservative metal;
   a polyethylenimine compound in an amount sufficient to form a chelation complex with the metal; and
   a vinyl based polymer selected from the group consisting of poly(vinyl alcohol), polyacrylamide, poly(N-vinyl pyrrolidone), poly(N-isopropyl acrylamide) and mixtures thereof;
   wherein no precipitate is present in the aqueous aqueous preservative composition and wherein said preservative composition is free of polyaspartic acid.

2. The composition of claim 1 further comprising an ammonia salt.

3. The composition of claim 1 further comprising ammonia.

4. The composition of claim 1 wherein the preservative metal is copper bearing material.

5. The composition of claim 4 wherein the copper bearing material is selected from the group consisting of copper metal, copper sulfate, copper acetate, copper formate, copper chloride, copper nitrate, basic copper carbonate, copper hydroxide, cupric oxide, cuprous oxide, copper borates and mixtures thereof.

6. The composition of claim 1 wherein the non-polymeric amine is selected from the group consisting of triethanolamine, ethylamine, diethylamine, ethylenediamine, ethanolamines having the following structural formula I:

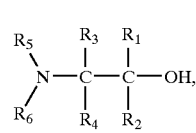

wherein $R_1$, $R_2$, $R_3$, $R_4$, $R_5$, $R_6$ independently=H, —$CH_3$, or —$C_2H_5$; and mixtures thereof.

7. The composition of claim 1 wherein the non-polymeric amine is present at a concentration between about 0.15% and about 10% by weight.

8. The composition of claim 1 wherein the non-polymeric amine is present at a concentration between about 0.15% and about 7.20% by weight.

9. The composition of claim 1 wherein the polyethylenimine compound has a molecular weight between about 100 and about 70,000.

10. The composition of claim 1 wherein the polyethylenimine compound is present at a concentration between about 0.01% and about 40.0% by weight.

11. The composition of claim 1 wherein the polyethylenimine compound is present at a concentration between about 0.1% and about 2.0% by weight.

12. The composition of claim 1 wherein the polyethylenimine compound is present at a concentration between about 0.01% and about 2% by weight.

13. The composition of claim 1 wherein the vinyl based polymer is present at a concentration between about 0.01% and about 8% by weight.

14. The composition of claim 1 wherein the vinyl based polymer is present at a concentration of from about 0.1% to about 1% by weight.

15. The composition of claim 1 further comprising a biocide.

16. The composition of claim 15 wherein the biocide is selected from the group consisting of fungicides, insecticides and mixtures thereof.

17. The composition of claim 16 wherein the fungicide is selected from the group consisting of azoles, quaternary ammonium compounds and mixtures thereof.

18. The composition of claim 1 wherein the cellulose based product is wood.

19. An aqueous preservative composition for treating a cellulose-based product, said composition comprising:
 between about 0.01% and about 15% by weight solubilized copper;
 between about 0.15% and about 10% by weight non-polymeric amine;
 between about 0.01% and about 40% by weight polyethylenimine having a number average molecular weight between about 100 and about 70,000; and
 between about 0.01% and about 8% poly(vinyl alcohol);
 wherein said aqueous preservative composition is free of polyaspartic acid.

20. The composition of claim 19 wherein the cellulose based product is wood.

21. A method for treating a cellulose based product, said method comprising:
 applying to the cellulose based product an aqueous preservative composition comprising:
  a preservative metal selected from the group consisting of copper, cobalt, aluminum, iron, lead, tin, cadmium, nickel, chromium, silver, zinc and mixtures thereof in a preservative amount;
  a non-polymeric amine compound in a solubilizing amount;
  a polyethylenimine compound in a chelation complex forming amount; and
  a vinyl based polymer selected from the group consisting of poly(vinyl alcohol), polyacrylamide, poly(N-vinyl pyrrolidone), poly(N-isopropyl acrylamide) and mixtures thereof;
 wherein no precipitate is present in the aqueous aqueous preservative composition, and wherein said preservative composition is free of polyaspartic acid.

22. The method of claim 21 wherein the aqueous preservative composition further comprises an ammonia salt.

23. The method of claim 21 wherein the aqueous preservative composition further comprises ammonia.

24. The method of claim 21 wherein the preservative metal is a copper bearing material.

25. The method of claim 24 wherein the copper bearing material is selected from the group consisting of copper metal, copper sulfate, copper acetate, copper formate, copper chloride, copper nitrate, basic copper carbonate, copper hydroxide, cupric oxide, cuprous oxide, copper borates and mixtures thereof.

26. The method of claim 21 wherein the non-polymeric amine is selected from the group consisting of triethanolamine, ethylamine, diethylamine, ethylenediamine, ethanolamines having the following structural formula I:

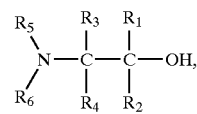

wherein $R_1$, $R_2$, $R_3$, $R_4$, $R_5$, $R_6$ independently=H, —$CH_3$, or —$C_2H_5$; and mixtures thereof.

27. The method of claim 21 wherein the polyethylenimine compound has a molecular weight between about 100 and about 70,000.

28. The method of claim 21 wherein the polyethylenimine compound is present at a concentration between about 0.01% and about 40.0% by weight.

29. The method of claim 21 wherein the polyethylenimine compound is present at a concentration between about 1.0% and about 40.0% by weight.

30. The method of claim 21 wherein the vinyl based polymer is present at a concentration between about 0.01% and about 8% by weight.

31. The method of claim 21 wherein the aqueous preservative composition further comprises a biocide.

32. The method of claim 31 wherein the biocide is selected from the group consisting of fungicides, insecticides and mixtures thereof.

33. The method of claim 32 wherein the fungicide is selected from the group consisting of azoles, quaternary ammonium compounds and mixtures thereof.

34. The method of claim 21 wherein the cellulose based product is flooded with the preservative composition under vacuum.

35. The composition of claim 21 wherein the cellulose based product is wood.

36. An aqueous preservative composition for treating a cellulose-based product, said composition comprising:
 a preservative metal selected from the group consisting of copper, cobalt, aluminum, iron, lead, tin, cadmium, nickel, chromium, silver, zinc and mixtures thereof in a preservative amount;
 one member of the group consisting of: a non-polymeric amine compound in an amount sufficient to solubilize the preservative metal and a polyethyleniniine compound in an amount sufficient to form a chelation complex with the metal; and
 a vinyl based polymer selected from the group consisting of poly(vinyl alcohol), polyacrylamide, poly(N-vinyl pyrrolidone), poly(N-isopropyl acrylamide) and mixtures thereof;
 wherein no precipitate is present in the aqueous preservative composition and wherein said aqueous preservative composition is free of polyaspartic acid.

37. The composition of claim 36 further comprising an ammonia salt.

38. The composition of claim 36 further comprising ammonia.

39. The composition of claim 36 wherein the preservative metal is copper bearing material.

40. The composition of claim 39 wherein the copper bearing material is selected from the group consisting of copper metal, copper sulfate, copper acetate, copper formate, copper chloride, copper nitrate, basic copper carbonate, copper hydroxide, cupric oxide, cuprous oxide, copper borates and mixtures thereof.

41. The composition of claim 36 wherein the non-polymeric amine is selected from the group consisting of triethanolamine, ethylamine, diethylamine, ethylenediamine, ethanolamines having the following structural formula I:

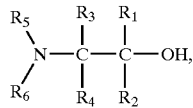

wherein $R_1, R_2, R_3, R_4, R_5, R_6$ independently=H, —$CH_3$, or —$C_2H_5$; and mixtures thereof.

42. The composition of claim 36 wherein the non-polymeric amine is present at a concentration between about 0.15% and about 50% by weight.

43. The composition of claim 36 wherein the non-polymeric amine is present at a concentration between about 0.15% and about 7.20% by weight.

44. The composition of claim 36 wherein the polyethylenimine compound has a molecular weight between about 100 and about 70,000.

45. The composition of claim 36 wherein the polyethylenimine compound is present at a concentration between about 0.01% and about 40.0% by weight.

46. The composition of claim 36 wherein the polyethylenimine compound is present at a concentration between about 0.1% and about 2.0% by weight.

47. The composition of claim 36 wherein the polyethylenimine compound is present at a concentration between about 0.01% and about 2% by weight.

48. The composition of claim 36 wherein the vinyl based polymer is present at a concentration between about 0.01% and about 30% by weight.

49. The composition of claim 36 wherein the vinyl based polymer is present at a concentration of from about 0.1% to about 1% by weight.

50. The composition of claim 36 further comprising a biocide.

51. The composition of claim 36 wherein the biocide is selected from the group consisting of fungicides, insecticides and mixtures thereof.

52. The composition of claim 36 wherein the fungicide is selected from the group consisting of azoles, quaternary ammonium compounds and mixtures thereof.

53. The composition of claim 36 wherein the cellulose based product is wood.

54. A method for treating a cellulose based product, said method comprising:
applying to the cellulose based product an aqueous preservative composition comprising:
a preservative metal selected from the group consisting of copper, cobalt, aluminum, iron, lead, tin, cadmium, nickel, chromium, silver, zinc and mixtures thereof in a preservative amount;
one member of the group consisting of: a non-polymeric amine compound in an amount sufficient to solubilize the preservative metal and a polyethylenimine compound in an amount sufficient to form a chelation complex with the metal; and
a vinyl based polymer selected from the group consisting of poly(vinyl alcohol), polyacrylamide, poly(N-vinyl pyrrolidone), poly(N-isopropyl acrylamide) and mixtures thereof;
wherein no precipitate is present in the aqueous preservative composition, and wherein said aqueous preservative composition is free of polyaspartic acid.

55. The method of claim 54 wherein the aqueous preservative composition further comprises an ammonia salt.

56. The method of claim 54 wherein the aqueous preservative composition further comprises ammonia.

57. The method of claim 54 wherein the preservative metal is a copper bearing material.

58. The method of claim 57 wherein the copper bearing material is selected from the group consisting of copper metal, copper sulfate, copper acetate, copper formate, copper chloride, copper nitrate, basic copper carbonate, copper hydroxide, cupric oxide, cuprous oxide, copper borates and mixtures thereof.

59. The method of claim 54 wherein the non-polymeric amine is selected from the group consisting of triethanolamine, ethylamine, diethylamine, ethylenediamine, ethanolamines having the following structural formula I:

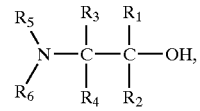

wherein $R_1, R_2, R_3, R_4, R_5, R_6$ independently=H, —$CH_3$, or —$C_2H_5$; and mixtures thereof.

60. The method of claim 54 wherein the polyethylenimine compound has a molecular weight between about 100 and about 70,000.

61. The method of claim 54 wherein the polyethylenimine compound is present at a concentration between about 0.01% and about 40.0% by weight.

62. The method of claim 54 wherein the polyethylenimine compound is present at a concentration between about 0.1% and about 2.0% by weight.

63. The composition of claim 54 wherein the non-polymeric amine is present at a concern between about 0.15% and about 50% by weight.

64. The composition of claim 54 wherein the non-polymeric amine is present at a concentration between about 0.15% and about 7.20% by weight.

65. The method of claim 54 wherein the vinyl based polymer is present at a concentration between about 0.01% and about 30% by weight.

66. The method of claim 54 wherein the aqueous preservative composition further comprises a biocide.

67. The method of claim 54 wherein the biocide is selected from the group consisting of fungicides, insecticides and mixtures thereof.

68. The method of claim 67 wherein the fungicide is selected from the group consisting of azoles, quaternary ammonium compounds and mixtures thereof.

69. The method of claim 54 wherein the cellulose based product is flooded with the preservative composition under vacuum.

70. The composition of claim 54 wherein the cellulose based product is wood.

* * * * *